(12) United States Patent
Weiss

(10) Patent No.: US 7,763,009 B1
(45) Date of Patent: Jul. 27, 2010

(54) TRI-FUNCTIONAL CANNULA FOR RETINAL ENDOVASCULAR SURGERY

(75) Inventor: Jonathan D. Weiss, Albuquerque, NM (US)

(73) Assignee: The United States of America as represented by the United States Department of Energy, Washington, DC (US)

( * ) Notice: Subject to any disclaimer, the term of this patent is extended or adjusted under 35 U.S.C. 154(b) by 92 days.

(21) Appl. No.: 12/034,142

(22) Filed: Feb. 20, 2008

(51) Int. Cl.
*A61M 31/00* (2006.01)
(52) U.S. Cl. .................................................. 604/507
(58) Field of Classification Search ............. 604/93.01, 604/264, 505–507, 521, 65–67, 500; 606/2, 606/2.5, 3, 4
See application file for complete search history.

(56) References Cited

U.S. PATENT DOCUMENTS

| | | | |
|---|---|---|---|
| 5,545,153 A | 8/1996 | Grinblat et al. | |
| 5,632,740 A | 5/1997 | Koch et al. | |
| 5,785,645 A | 7/1998 | Scheller | |
| 5,836,940 A | 11/1998 | Gregory | |
| 6,355,027 B1 | 3/2002 | Le et al. | |
| 6,402,734 B1 | 6/2002 | Weiss | |
| 6,916,000 B2 | 7/2005 | Weiss | |
| 6,936,053 B1 * | 8/2005 | Weiss | .................... 606/107 |
| 7,217,263 B2 | 5/2007 | Humayun et al. | |
| 2007/0021653 A1 | 1/2007 | Hattenbach et al. | |
| 2007/0211212 A1 | 9/2007 | Bennwik | |

* cited by examiner

*Primary Examiner*—Nicholas D Lucchesi
*Assistant Examiner*—Theodore J Stigell
(74) *Attorney, Agent, or Firm*—Arthur N. Trausch; James C. Durkis

(57) ABSTRACT

A tri-functional cannula combines the functions of tissue Plasminogen Activator (tPA) solution delivery, illumination and venous pressure measurement. The cannula utilizes a tapered hollow-core optical fiber having an inlet for tPA solution, an attached fiber optic splitter configured to receive illumination light from an optical source such and a LED. A window in the cannula transmits the light to and from a central retinal vein. The return light is coupled to an optical detector to measure the pressure within the vein and determine whether an occlusion has been removed.

10 Claims, 1 Drawing Sheet

TRI-FUNCTIONAL CANNULA FOR RETINAL ENDOVASCULAR SURGERY

The United States Government has rights in this invention pursuant to Contract No. DE-AC04-94-AL85000 between the United States Department National Nuclear Security Administration and Sandia Corporation for the operation of Sandia National Laboratories.

BACKGROUND OF THE INVENTION

1. Field of the Invention

The present invention relates to surgical procedures that alleviate central retinal vein occlusion (CRVO), and more specifically, it relates to a multifunctional cannula for use in such CRVO procedures.

2. Description of Related Art

The central retinal vein (retinal vein) is a short vein that runs through the optic nerve and drains blood from the capillaries of the retina into the larger veins outside the eye. The anatomy of the veins of the orbit of the eye varies between individuals, and in some the central retinal vein drains into the superior ophthalmic vein, and in some it drains directly into the cavernous sinus. The central retinal vein is the venous equivalent of the central retinal artery, and like that blood vessel, can suffer from occlusion (central retinal vein occlusion), similar to that seen in ocular ischemic syndrome. Since the central retinal artery and vein are the sole source of blood supply and drainage for the retina, such occlusion can lead to severe damage to the retina and blindness.

Each year, about 60,000 people in the United States experience a blockage of the major exit vein of one of their eyes. Worldwide, this number is, undoubtedly, many times larger. The blockage decreases blood flow to the retina which results in a significant reduction of oxygen to the visual cells in the retina, causing vision impairment. The visual field becomes blurry or worse and is reduced to a yellow formless disc. If blood flow is severely impaired, blindness can ensue. This condition is formally known as "Central Retinal Vein Occlusion" (CRVO).

A refinement of a surgical procedure that has been recently created by an ophthalmologist is desired to alleviate this condition. The procedure currently requires three incisions into the eye and the injection through one of the incisions of a blood clot dissolver, known as tissue Plasminogen Activator (tPA), into one of the retinal branch veins. The purpose each of the three incisions are to (i) illuminate the retina, (ii) insert a syringe needle (more properly, a cannula) for delivery of the tPA solution and (iii) remove the vitreous humor and its replace it with a saline solution.

A number of issues arise when utilizing tPA to remove a central retinal vein occlusion. It is unclear whether the tPA works by dissolving the clot chemically, or if the overpressure caused by the injection dislodges the jet mechanically. If the latter is the case, then the clot may reattach itself elsewhere in the body. If the pressure in the retinal system of veins could be measured during the tPA injection, then a sudden drop in pressure suddenly during injection would indicate that the clot was probably dislodged. The problem is how to measure the pressure in the retinal system of veins. If the pressure is measured in the syringe pump outside the eye, changes downstream of the cannula may not be observable, given the high impedance to flow presented by its narrow tip. If pressure downstream of the cannula cannot be monitored while the tPA solution is being injected, an apparatus that can stop the injection for a reasonable length of time during the procedure (about 30 seconds) for pressure equalization to take place between the vein and the pump is desired so that an accurate measurement can be performed.

Although the prior art procedure is often effective, it is desirable to reduce the number of incisions and to overcome the apparent issues.

SUMMARY OF THE INVENTION

It is an object of the present invention to provide a tri-functional cannula that combines the functions of tissue Plasminogen Activator (tPA) solution delivery, illumination and venous pressure measurement.

This and other objects will be apparent based on the disclosure herein.

The invention is a multi-functional cannula. A tri-functional embodiment combines tPA solution delivery, illumination and venous pressure measurement. It is possible to combine the light delivery function with the tPA solution delivery function of the cannula because the tPA liquid allows transmission in the visible region of the electromagnetic spectrum. The illumination light is further utilized to measure pressure within the central retinal vein.

The tri-functional embodiment is a cannula formed from a tapered hollow-core optical fiber. The interior of the tapered hollow-core optical fiber is also used to channel tPA. An exemplary type of tapered hollow-core optical fiber consists of a pure silica-core tube, the inside of which is coated with highly reflecting silver and a clear silver iodide layer to enhance that reflectivity. One example type is manufactured for more conventional optical purposes by Polymicro Technologies, a specialty fiber-optics company in Phoenix that licensed the technology from the Fiber-Optic Materials Research Program of Rutgers University. Such a fiber is modifiable for the present device by, for example, adding a taper that is similar to the one now used with an existing cannula used for the surgery described in the Description of Related Art above.

In the surgical procedure for correction of CRVO, a pressure measurement taken outside of the eye may not detect changes downstream of the cannula due to a high impedance to flow presented by a narrow cannula tip. Often, pressure downstream of the cannula cannot be monitored while the tPA solution is being injected. To overcome these issues, pressure sensing has been added as a third function of the cannula to obtain, in real-time, local pressure measurements within the branch vein into which the tPA solution is being injected. For safety reasons, the sensor is optical, rather than electrical. This "tri-functionality" of the cannula is accomplished with no added instrumental size or complexity within the eye. All components that take up space are positioned outside of the eye, where space and biocompatibility are not an issue.

The present invention include a means of measuring the venous pressure just beyond the tip of the hollow-core optical cannula. This is accomplished in an embodiment of the present invention by utilizing the light that reflects off the interior wall of the vein and returns to the cannula. The vein will expand under pressure; thus, the curvature of its interior wall will change. This change will affect the optical power returning to the cannula and guided back to the source. In some cases, the reflective properties of the wall will change under expansion because it is not a simple inorganic structure. Thus, there will be a relationship between the local pressure and the return signal. Whether or not the light used for illumination could also be used for this purpose depends on the wavelength dependence of the optical properties of the wall. If right of a different wavelength is needed, it can be sent down the cannula simultaneously. The detection of the return signal complicates the back end of the cannula, but few space constraints are present there. Hence, the cannula becomes a tri-functional device.

Sterility of the tPA is maintained by isolating it from the optical and mechanical components needed to bring light to this unconventional syringe. A window is thus provided within the syringe, usually near its far end, which allows for the passage of light, while providing physical isolation for the tPA solution. An optical fiber then carries the light to the back of the cannula, although a light source can be connected directly. In one embodiment, the tPA solution enters the syringe needle from the side.

BRIEF DESCRIPTION OF THE DRAWINGS

The accompanying drawing, which is incorporated into and forms a part of the disclosure, illustrates an embodiment of the invention and, together with the description, serve to explain the principles of the invention.

DETAILED DESCRIPTION OF THE INVENTION

Figure 1:
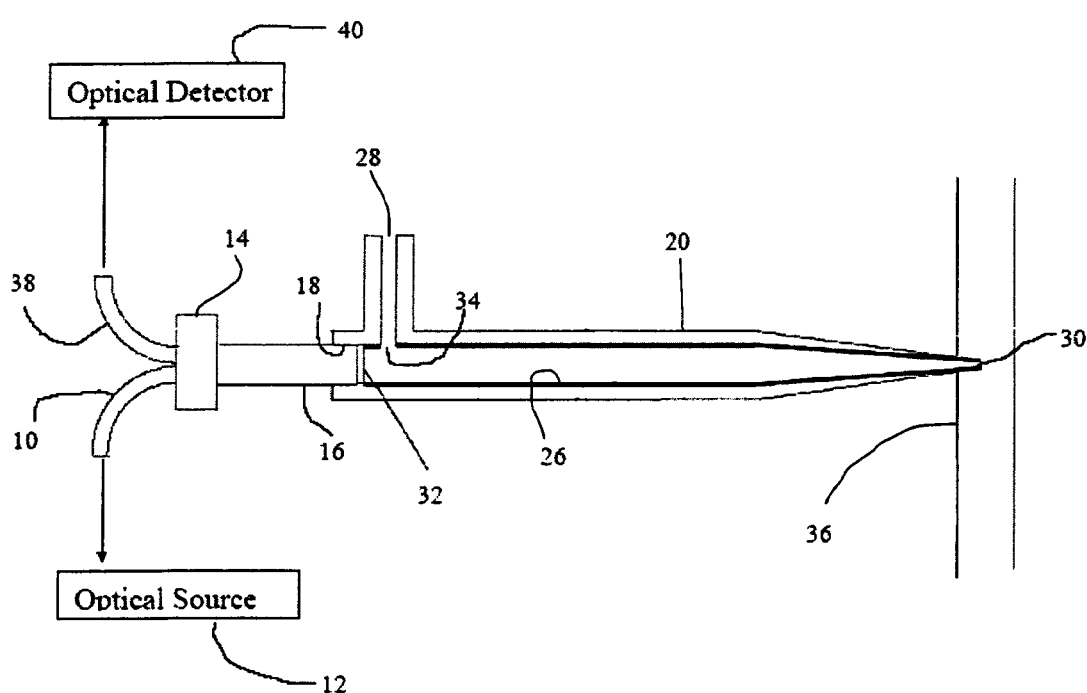
FIG. 1 shows an exemplary tri-functional cannula that utilizes a tapered hollow-core optical fiber having an inlet for tPA solution, a window and a fiber optic splitter configured to receive illumination light from an optical source such and a LED and to transmit light to an optical detector to facilitate measurement of pressure within the central retinal vein. The taper need not be linear, as is shown in the figure. At the far end, it could be more gradual, as is done now with a glass syringe that just delivers the tPA solution.

The invention is a multi-functional cannula. FIG. 1 shows an exemplary tri-functional embodiment that combines the functions of tissue Plasminogen. Activator (tPA) solution delivery, illumination and venous pressure measurement. Fiber optic 10 is configured to receive input light from an optical source 12. Fiber optic 10 is coupled to a fiber optic splitter 14, which is coupled to at least one fiber optic within a sheath 16. The fiber optic may alternately comprise a plurality of fiber optics or a fiber optic bundle. The end of sheath 16 is attached within an inner sleeve 18 of a cannula 20, which is shown in cross-section. Cannula 20 is formed from a capillary into a tapered hollow-core optical fiber, which includes a reflective inner wall 26. Cannula 20 includes an inlet port 28 and an outlet port 30. A window 32 abutting or in contact with the reflective inner wall 26 is provided in the inner sleeve 18 near the end of the optical fibers within sheath 16. Reflective inner wall 26 includes an opening 34. Inlet port 28 and opening 34 allow the flow of tPA solution through cannula and through outlet port 30 and into a vein 36. Fiber optic 38 is configured to receive output light collected by the fiber optic or fiber optic bundle that is located within sheath 16. Optical detector 40 is configured to receive light from fiber optic 38.

Illumination from the optical source 12 can be provided from a variety of sources. For example, a light emitting diode (LED) can be connected to fiber optic 10. Exemplary LED light sources are discussed in U.S. Pat. No. 5,008,718, incorporated herein by reference. The patent describes a light-emitting diode having active p-n junction layers of AlGaInP overlain by a transparent window layer of semiconductor different from AlGaInP, with a low resistivity and a bandgap greater than the active layers, so that the overlying layer is transparent to light emitted by the p-n junction. Suitable materials include AlGaAs, GaAsP, and GaP. Another exemplary light source is a light emitting semiconductor device having a wafer-bond layer as described in U.S. Pat. No. 5,502, 316, incorporated herein by reference. A "wafer bond layer" is defined therein as a layer or substrate that exhibits the properties that are characteristic of a layer that has undergone wafer bonding. It is believed that one such characteristic is a different nature of misfit dislocations formed at the wafer bonded interface, compared to an epitaxially grown mismatched heterointerface. An interface that has undergone wafer bonding has been observed to exhibit misfit dislocations which primarily consist of "edge dislocations," i.e., dislocations whose Burgers vector lies in the plane of the wafer bonded interface. These properties are in contrast to an epitaxially grown mismatched interface, which typically exhibits a much higher density of "threading dislocations," i.e., dislocations which are not confined to the plane of the mismatched interface and tend to propagate perpendicular to the interface. Other white light sources could be used to provide illumination. Non-white sources and single or narrow band frequencies of light may be usable in other applications that utilize the same device described herein. In one embodiment, the light source is connected directly to the cannula 20. An LED can be connected into inner sleeve 18 of cannula 20. Fiber optics, fiber optic splitters and fiber bundles are well known and commercially available from a large number of sources. Exemplary fiber optic splitters are described in the following patents, which are incorporated herein by reference: (i) U.S. Pat. No. 7,277,620, titled: "Fiber optic splitter", (ii) U.S. Pat. No. 6,865,332, titled: "Fiber optic splitter package and method of manufacture" and (iii) U.S. Pat. No. 4,431, 261, titled: "Fiber optic splitter".

Cannula 20 can be manufactured into a tapered hollow-core fiber optic from a capillary tube such as a pure silica-core tube. Exemplary starting dimensions for such a tube can be selected to be 1000 μm ID and 1300 μm OD. The cannula length is not critical and can be selected according to the preference of a user. A typical length is two to five inches. The inside lumen of this pure silica-core tube is coated with highly reflecting silver and a clear silver iodide to form reflective inner wall 26. Other coatings are usable as well, depending upon the desired reflectivity at a particular wavelength. The reflective inner wall may be adhered to the capillary with an epoxy or may be deposited directly onto the glass. A clear biocompadble sealant may be coated over the reflective inner wall. The capillary is then pulled or drawn down to a suitable taper. An exemplary taper has a 50 μm ID (for outlet port 30) and a 70 μm OD.

The inlet 28 of cannula 20 can be formed from a silica-core tube that has a 500 μm ID and a 1000 μm OD. An opening 34 having a diameter of about 500 μm is made in the tapered cannula near the end opposite to the tapered end. (In some embodiments, the silica tube of the cannula may include an outer coating of acrylate. In such cases, the acrylate can be removed prior to the connection of the inlet 28.) The inlet 28 can be attached to the cannula 20 such that the ID of the inlet 28 aligns with opening 34. The inlet capillary can be attached to the cannula with epoxy or an end can be heated to its melting point allowing the molten silica to form a bond with the cannula.

Window 32 is affixed into inner sleeve 18 so that the reflective inner wall 26 abuts (skirts) the outer edge of the window along its entire circumference. An exemplary window is made of silica, is 250 μm to 500 μm thick and is hermetically sealed to the inner sleeve. This window allows for the transmission of light and closes the proximal end opening of the capillary, leaving only one open path, which is located between the inlet 28 and the outlet 30 for movement of the tPA solution. The tPA solution is clear to visible wavelengths, enabling the transmission of visible light which is used by the surgeon to illumination the area.

A third function that can be combined into the tapered cannula of the present invention is the measurement of venous pressure just beyond the tip of the hollow-core optical cannula. This is accomplished by measuring the intensity change of the light that reflects off the interior wall of the vein and returns through the cannula to the optical detector 40. The vein will expand under pressure; thus, the curvature of its interior wall will change. This change will affect the optical power returning to the cannula. The reflective properties of the wall may change under expansion because it is not a simple inorganic structure. Thus, there will be a relationship between the local pressure and the return signal.

In operation, the cannula-device can be pre-calibrated (calibrated prior to insertion into a vein) such that the amount of detected light is correlated to a particular pressure and a particular vein curvature. A calibration chart can be made that shows whether the light increases or decreases with pressure changes. Once the cannula tip is inserted into the vein, the light level can be read and the pressure determined. Further, once the tip has been inserted into the vein, the tPA solution can be slowly injected, with the purpose of dissolving or dislodging a suspected clot or obstruction. A relatively large change in pressure will occur when the occlusion is removed. This will usually result in a decreased pressure and an increase in the detected light. An exemplary detector 40 for use in this application is a, silicon PIN photodiode.

The pressure-sensor wavelength could be different from the illumination wavelength and need not be in the visible. It could be in the infrared. The two could be separated with optical filters such that the illumination wavelength does not reach the photo-detector. Also, the sensor light could be modulated at a well-defined frequency (like 10 kHz) and the signal detected at that frequency to further filter out unwanted signals. On the other hand, a single light source could be used and modulated at a given frequency. The light output would consist of a modulated and a steady component, which could be separated from each other by electrical filtering.

The annular region of the tube itself can be used as a waveguide to transmit the illumination signal. Annular core waveguides have been studied, although not widely used. The light would be guided by the glass-air interface on the outer surface and reflective surface (glass-silver) on the inside. Within the tapered portion region, the light will tend to "spill" out of the guide on the outer surface due to the geometrical change. (This happens with tapered waveguides, in general). This property can improve the illumination of the interior of the eyeball and will allow illumination while the end of the cannula is inserted into the vein.

Sapphire, aluminum oxide, has a refractive index that is less than one in the wavelength region from about 10 microns to about 17 microns. Glass lenses are made of sapphire for use in the visible and near infrared because the material is so resistant to corrosion. Ordinary glass, including the purest silica, will not transmit at 10 microns. For light to be wave guided in a certain region of space, it has to be surrounded by a medium of lower refractive index. Thus, at 10.6 microns, the wavelength of the $CO_2$ laser, the light can be guided by air surrounded by sapphire. This wavelength could be used for pressure sensing. Visible light, for illumination, could be sent down the annular body of the sapphire and be guided by the sapphire-air interface, as mentioned above. Thus, the addition of a reflective inner surface would be unnecessary. Basically, the cannula would look the same. There are fibers for infrared transmission (10 and 38 in FIG. 1) including the hollow-core waveguide, chalcogenide (made of AsGeSeTe) fibers and fibers made of a combination of silver, bromine, and chlorine. Detectors for that wavelength also exist ("MCT" from Judson Technologies, for example, which is a semiconductor made of mercury, cadmium, and tellurium). The visible portion of the spectrum is easily taken care of by standard silicon detectors and conventional glass or plastic fibers.

The foregoing description of the invention has been presented for purposes of illustration and description and is not intended to be exhaustive or to limit the invention to the precise form disclosed. Many modifications and variations are possible in light of the above teaching. The embodiments disclosed were meant only to explain the principles of the invention and its practical application to thereby enable others skilled in the art to best use the invention in various embodiments and with various modifications suited to the particular use contemplated. The scope of the invention is to be defined by the following claims.

I claim:

1. A method, comprising:
    providing a hollow length of material comprising an inner wall that is reflective to at least one wavelength of the electromagnetic spectrum, wherein said length of material comprises a proximal end and a distal end, wherein said distal end comprises a taper;
    optically coupling light comprising said at least one wavelength into said proximal end;
    inserting a portion of said taper into a vein having a fluid pressure; and
    transmitting the light through the distal end of the hollow length of material into the vein, wherein the light reflects off an interior wall of the vein and returns to the proximal end of the hollow length of material; and
    measuring a change in intensity of the light returning to the proximal end and determining a change in fluid pressure in the vein just beyond the distal end of the hollow length of material.

2. The method of claim 1, further comprising flowing a solution through said hollow length of material concurrently with the transmission of light such that said solution will only exit said hollow length of material at said distal end.

3. The method of claim 1, wherein a window is attached within said hollow length of material near said proximal end, wherein said window is at least partially optically transmissive at said at least one wavelength.

4. The method of claim 3, wherein said vein comprises a central retinal vein.

5. The method of claim 3, further comprising injecting a solution of tPA into said hollow length of material.

6. The method of claim 3, wherein said hollow length of material comprises a lumen, wherein said hollow length of material further comprises a solution inlet into said lumen.

7. The method of claim 1, wherein said hollow length of material comprises a capillary tube.

8. The method of claim 1, wherein said hollow length of material comprises a tapered hollow-core optical fiber.

9. The method of claim 1, wherein said inner wall comprises a reflective coating that is reflective to said at least one wavelength.

10. The method of claim 9, wherein said reflective coating comprises silver.

* * * * *